United States Patent [19]

Mikkelsen et al.

[11] Patent Number: 5,674,833
[45] Date of Patent: Oct. 7, 1997

[54] DETERGENT COMPOSITIONS CONTAINING PROTEASE AND NOVEL INHIBITORS FOR USE THEREIN

[75] Inventors: Jan Møller Mikkelsen, Gentofte; Allan Svendsen; Børge Diderichsen, both of Birkerød; Ib Groth Clausen, Charlottenlund, all of Denmark

[73] Assignee: Novo Nordisk A/S, Novo Alle, Denmark

[21] Appl. No.: 435,241

[22] Filed: May 5, 1995

Related U.S. Application Data

[63] Continuation of Ser. No. 827,688, filed as PCT/DK91/00279, Sep. 18, 1991, abandoned.

[30] Foreign Application Priority Data

Sep. 18, 1990 [DK] Denmark ................................ 2237/90

[51] Int. Cl.[6] ........................................................ C11D 3/386
[52] U.S. Cl. ........................ 510/530; 210/393; 210/392; 435/188; 435/219; 435/220; 435/221; 435/222; 435/264; 435/320.1; 435/69.1
[58] Field of Search ...................... 252/174.12, DIG. 12; 435/188, 219–222, 264, 320.1, 69.1; 510/392, 530, 393

[56] References Cited

U.S. PATENT DOCUMENTS 5,071,586  12/1991  Kaiserman et al. .................. 510/393
5,527,487   6/1996  Mikkelsen et al. .................. 510/393

FOREIGN PATENT DOCUMENTS 0 332 576  9/1989  European Pat. Off. .

OTHER PUBLICATIONS

Hirono et al. J. Mol. Biol. vol. 178 pp. 389–413 published 1984.

Longstaff et al., Biochemistry, vol. 29, No. 31, pp. 7339–7347 (1990).

*Primary Examiner*—Douglas J. McGinty
*Assistant Examiner*—Kery A. Fries
*Attorney, Agent, or Firm*—Steve T. Zelson, Esq.; Elias J. Lambiris, Esq.

[57] ABSTRACT

A detergent composition and additive comprising a protease and a reversible protease inhibitor of the peptide or protein type, wherein the ratio of the dissociation constant to the protease concentration in the range from 0.006 to 6. When the protease is subtilisin, the protease inhibitor is preferably a modified subtilisin inhibitor of Family VI.

27 Claims, 3 Drawing Sheets

DETERGENT COMPOSITIONS CONTAINING PROTEASE AND NOVEL INHIBITORS FOR USE THEREIN

This application is a continuation of application Ser. No. 07/827,688 filed Jan. 28, 1992, now abandoned, which is a continuation of Ser. No. PCT/DK91/00279 filed Sep. 18, 1991, the contents of which are incorporated herein by reference.

TECHNICAL FIELD

This invention relates to an improved detergent composition comprising a protease (particularly a subtilisin) and a reversible protease inhibitor of peptide or protein type, to a detergent additive comprising such a protease and inhibitor and to a method for stabilizing a protease.

The invention also relates to novel modified subtilisin inhibitors for use in said detergent, to a recombinant DNA molecule comprising a nucleotide sequence coding for the modified subtilisin inhibitor, to a transformed host organism comprising the DNA and to a method of producing the modified inhibitor.

BACKGROUND ART

Proteases, especially subtilisins, are widely used as ingredients in commercial detergents. A major problem in formulating protease-containing detergents, especially liquid detergents, is that of ensuring enzyme stability during storage.

The prior art has dealt extensively with improving the storage stability. As an example, JP-A 62-269689 demonstrates improvement of the stability of a protease (e.g. a subtilisin) in a liquid detergent by incorporation of a protease inhibitor of protein type. As stated in said publication, the protease inhibitor should ideally show essentially no inhibiting effect under dilute washing conditions, i.e. when the detergent is in use.

STATEMENT OF THE INVENTION

We have found that in the known detergents containing protease and inhibitor, the protease is almost totally inhibited under dilute washing conditions. We have also found that by a suitable choice of inhibitor for a given protease, it is possible to essentially avoid inhibition at the dilute conditions of washing, while still achieving effective enzyme stabilization in the detergent during storage.

We have also found that subtilisin inhibitors with this improved performance can be derived from known inhibitors by substituting certain amino acids. The novel inhibitors can be produced by known genetic engineering methods.

Accordingly, the invention provides a detergent composition comprising a protease and a reversible protease inhibitor of peptide or protein type, characterized in that the ratio of the dissociation constant to the protease concentration is in the range from 0.006 to 6, or that the dissociation constant is in the range from 0.05 to 50 µM. The invention also provides a detergent additive comprising protease in the form of a stabilized liquid or a non-dusting granulate, characterized by further comprising a reversible protease inhibitor of peptide or protein type having an dissociation constant in the above range. Further, the invention provides a method for stabilizing a protease by incorporation of a protease inhibitor as described.

Another aspect of the invention provides a detergent composition and a detergent additive comprising a subtilisin, characterized by further comprising a modified subtilisin inhibitor of Family VI having one or more of the following amino acid substitutions at the indicated position:

P6: Ala, Glu or Lys,
P5: Gly, Val, Leu or Pro
P4: Val, Pro, Trp, Ser, Glu or Arg,
P3: Tyr, Glu, Ala, Arg, Pro, Ser, Lys or Trp,
P2: Ser, Lys, Arg, Pro, Glu, Val, Tyr, Trp or Ala,
P1: Arg, Tyr, Pro, Trp, Glu, Val, Ser, Lys or Ala,
P'1: Gln, Ser, Thr, Ile, Lys, or Pro,
P'2: Val, Glu, Arg, Pro or Trp,
P'3: Glu, Gln, Asn, Val, Phe or Tyr.

The invention also provides a modified subtilisin inhibitor of family VI, as defined above, excluding:

Eglin B and C substituted with Ser or Pro at position 44 (P2), Leu, Arg, Phe, Tyr at 45 (P1) or Glu, Ser or Thr at 46 (P'1), Eglin C substituted with Arg45, Ser46 and CI-2 substituted with Tyr, Ala or Lys at 59 (P1).

Further, the invention provides a recombinant DNA molecule comprising a nucleotide sequence coding for a modified subtilisin inhibitor as defined above, a transformed host organism comprising this DNA and a method of producing the modified inhibitor comprising cultivation of this transformed host organism.

Modified subtilisin inhibitors of family VI are known (EP 332,576, C. Langstaff et al., *Biochemistry*, 1990, 29, 7339–7347), but their use in detergents and the resulting advantages have not been disclosed or suggested.

DETAILED DESCRIPTION OF THE INVENTION

Protease

Figure 1:
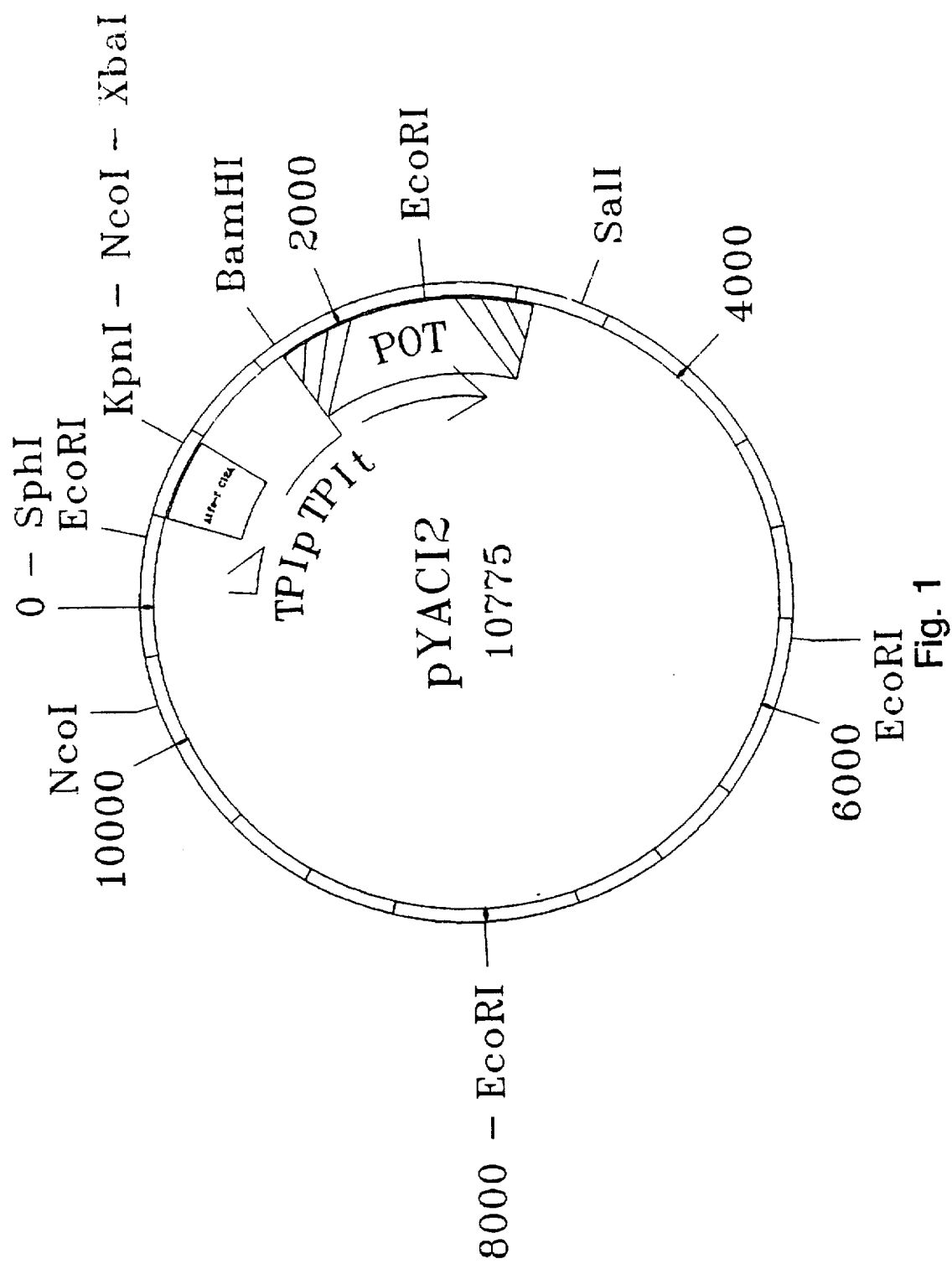
FIG. 1 shows a map of the expression plasmid pYACI2.

The protease used in the invention is preferably of microbial origin. It may be a serine protease, preferably an alkaline microbial protease or a trypsin-like protease. Examples of alkaline proteases are subtilisins, especially those derived from Bacillus, e.g. subtilisin Novo, subtilisin Carlsberg, subtilisin 309, subtilisin 147 and subtilisin 168 (both described in WO 89/06279) and mutant subtilisins such as those described in WO 89/06279 and DK 0541/90. Examples of commercial Bacillus subtilisins are Alcalase®, Savinase® and Esperase®, products of Novo Nordisk A/S. Examples of trypsin-like proteases are trypsin (e.g. of porcine or bovine origin) and the *Fusarium* protease described in WO 89/06270.

The amount of protease in the detergent will typically be 0.2–40 µM especially 1–20 µM (generally 5–1000 mg/l, especially 20–500 mg/l) as pure enzyme protein.

Inhibitor

According to the invention, the inhibitor is chosen for a given detergent (protease type and concentration etc.) so that the dissociation constant ($K_d$) is high enough to allow adequate release of protease when the detergent is diluted with water, yet the dissociation constant is low enough to allow efficient inhibition in the concentrated detergent during storage. $K_d$ is commonly defined for a given protease and a given inhibitor in a given system as the equilibrium constant $$K_d = [E]*[I]/[EI]$$

the reactive site, amino acid positions are numbered P1, P2 etc. in the direction of the N-terminal and P'1, P'2 etc towards the C-terminal.

| Inhibitor | P6 | P5 | P4 | P3 | P2 | P1 | P'1 | P'2 | P'3 | |
|---|---|---|---|---|---|---|---|---|---|---|
| CI-1 | Asp | Ala | Met | Val | His | Leu | Asn | Phe | Asp | (SEQ ID NO: 5) |
| CI-2 | Gly | Thr | Ile | Val | Thr | Met | Glu | Tyr | Arg | (SEQ ID NO: 6) |
| PSI | Gly | Ser | Pro | Val | Thr | Met | Asp | Phe | Arg | (SEQ ID NO: 7) |
| Eglin C | Gly | Ser | Pro | Val | Thr | Leu | Asp | Leu | Arg | (SEQ ID NO: 8) |
| Eglin B | Gly | Ser | Pro | Val | Thr | Leu | Asp | Leu | Arg | (SEQ ID NO: 9) |
| TSI-1 | Gly | Ser | Pro | Ile | Thr | Leu | Asp | Tyr | Leu | (SEQ ID NO: 10) |
| VSI | Gly | Ser | Phe | Val | Thr | Ala | Asp | Tyr | Lys | (SEQ ID NO: 11) |
| Variation | | | | | | | | | | |
| | Asp | Ala | Met | Val | His | Leu | Asn | Phe | Asp | |
| | Gly | Thr | Ile | Ile | Thr | Met | Glu | Tyr | Arg | |
| | | Ser | Pro | | | Ala | Asp | Leu | Leu | |
| | | | Phe | | | | | | Lys | |
| Modifications according to invention | | | | | | | | | | |
| | Ala | Gly | Val | Tyr | Ser | Arg | Gln | Val | Glu | |
| | Glu | Val | Pro | Glu | Lys | Glu | Ser | Glu | Gln | |
| | Lys | Leu | Trp | Ala | Arg | Val | Pro | Arg | Asn | |
| | | Pro | Ser | Arg | Pro | Ser | Ile | Pro | Val | |
| | | | Glu | Pro | Glu | Lys | Thr | Trp | Phe | |
| | | | Arg | Ser | Val | Tyr | Lys | | Tyr | |
| | | | | | Lys | Tyr | Pro | | | |
| | | | | | Trp | Trp | Ala | | | |
| | | | | | | Ala | Trp | | | | where the square brackets indicate molar concentration of free enzyme (E), free inhibitor (I) and enzyme-inhibitor complex (EI), respectively.

The ratio of the dissociation constant to the protease concentration is preferably from 0.06 to 6. The dissociation constant is preferably from 1 to 10 μM (i.e. $10^{-6}$–$10^{-5}$ M).

The desired $K_d$ is achieved by suitable selection of protease and inhibitor. The inhibitor may be one of the novel modified inhibitors provided by the invention, or it may be selected from among the many known inhibitors, e.g. Streptomyces subtilisin inhibitor used together with trypsin. See e.g. Lakowski, Jr. & Kato, Ann. Rev. Biochem. 49:593–626 (1980) and S. Murao et al., in *Protein Protease Inhibitor— The Case of Streptomyces Subtilisin Inhibitor* (1985) at pp. 1–14 for a general description of known inhibitors.

The amount of inhibitor is preferably such that the molar ratio of inhibitor reactive site to protease active site is above 0.6, preferably 1–10.

Novel Inhibitor

The novel inhibitors provided by the invention are derived from the known inhibitors of Family VI, described in the above references, e.g. from barley subtilisin inhibitor CI-1 or CI-2, potato subtilisin inhibitor (PSI) Eglin B or C, tomato subtilisin inhibitor or Vicia subtilisin inhibitor (VSI).

Inhibitors of this family are known to strongly inhibit the subtilisins commonly used in detergents, with inhibitor dissociation constants generally below $10^{-10}$ M. We have found that by using these inhibitors to stabilize a protease in a detergent, the protease is so strongly bound that very little protease activity is released when the detergent is diluted for use in washing, and the protease remains almost completely inactive. We have therefore realized a need for a modified inhibitor with weaker binding to the protease.

The following shows a comparison of the sequences in the binding region of some family VI inhibitors. Starting from It appears that the inhibitors show a marked homology in the binding region. We have now found that the protease-inhibitor binding can be suitably weakened by substituting one or more of these amino acids, e.g. with one that is not represented at that position, i.e. with one that has a different side chain length and/or is differently charged from those represented. The modified inhibitors are resistant to hydrolysis by the protease.

A preferred inhibitor is CI-2 substituted with Arg, Pro or Glu at position P3, Lys or Arg at P2, and/or Glu, Arg or Pro at P1. Another preferred inhibitor is PSI substituted with Tyr at P3, Lys or Arg at P2, Arg, Tyr or His at P1 and/or Trp at P'1.

The novel inhibitors may be produced by known genetic engineering techniques. Briefly, a DNA sequence (cDNA or a synthetic gene) encoding a known inhibitor is subjected to mutagenesis in order to replace the codon(s) for the amino acid(s) to be substituted with a new codon (codons) for the desired amino acid substitution(s). This may preferably be carried out by oligonucleotide-directed site-specific mutagenesis in bacteriophage M13 vectors (e.g. M. J. Zoller and M. Smith, Meth. Enzymol. 100 (1983) 468–500), in double-stranded DNA vectors (e.g. Y. Morinaga et al., Biotechnology (July 1984) 636–639), or by the polymerase chain reaction (PCR) (e.g. R. Higuchi, Nucl. Acids. Res. 16 (1988) 7351–7367).

The mutant gene is subsequently expressed in a suitable host strain. Suitable hosts are bacteria (e.g. strains of *Escherichia coli* or Bacillus), fungi (e.g. strains of *Saccharomyces cerevisiae* or filamentous fungi like Aspergillus), plants such as tomato or potato or established human or animal cell lines. To accomplish expression, the mutant gene has to be inserted in an expression plasmid with promoter and terminator DNA elements for the formation of translatable mutant inhibitor mRNA in vivo. The plasmid is introduced into the host by genetic transformation. The choice of expression plasmid is dependent on the type of host strain used. The expression of the mutant inhibitor may be done intracellularly or extracellularly. In the latter case, the DNA sequence coding for the mutant inhibitor is fused in frame to a DNA sequence encoding a suitable peptide signalling secretion. The secretion signal should preferably be cleaved off in vivo, resulting in secretion of the mature mutant inhibitor into the growth medium.

Various species of Bacilli, including *Bacillus alkalophilus, B. amyloliquefaciens, B. brevis, B. lentus, B. licheniformis, B. megaterium, B. stearothermophilus*, and *B. subtilis*, are known to secrete proteins efficiently. In many cases this has also been shown to be the case for heterologous proteins. Since expression of a secreted protease inhibitor has the potential advantage of facilitating purification, it is obviously interesting to attempt to express the inhibitor as a secreted product from a Bacillus strain. This could for instance be accomplished by combining the structural part of the inhibitor with the promoter and signal peptide of a well expressed and secreted Bacillus enzyme as for instance the maltogenic amylase from *B. stearothermophilus* (Diderichsen, B. and Christiansen, L. Cloning of a maltogenic alpha-amylase from *Bacillus stearothermophilus*, FEMS Microbiol. Lett. 56:53–60, 1988) or the alpha-amylase from *B. licheniformis* (Jørgensen, P. L., C. K. Hansen, G. B. Poulsen and B. Diderichsen. In vivo genetic engineering: Homologous recombination as a tool for plasmid construction, GENE 96: 37–41, 1990). This may be accomplished in many ways as known by people skilled in the art. One way is to use in vivo genetic engineering (Jørgensen et al. 1990, op. cit.). The advantage of this method is that it easily generates a perfect fusion between signal peptide and mature inhibitor which according to well documented rules for signal peptide processing would be expected to give the correct N-terminal amino acid residue of the inhibitor.

In one method of producing barley CI-2 inhibitor and variants hereof, a filamentous fungus is used as the host organism. The filamentous fungus host organism may conveniently be one which has previously been used as a host for producing recombinant proteins, e.g. a strain of *Aspergillus sp.*, such as *A. niger, A. nidulans* or *A. oryzae*. The use of *A. oryzae* in the production of recombinant proteins is extensively described in, e.g. EP 238 023.

For expression of CI-2 inhibitor and variants in Aspergillus, the DNA sequence encoding the protease inhibitor is preceded by a promoter. The promoter may be any DNA sequence exhibiting a strong transcriptional activity in Aspergillus and may be derived from a gene encoding an extracellular or intracellular protein such as an amylase, a glucoamylase, a protease, a lipase, a cellulase or a glycolytic enzyme.

Examples of suitable promoters are those derived from the gene encoding *A. oryzae* TAKA amylase, *Rhizomucor miehei* aspartic proteinase, *A. niger* neutral alpha-amylase, *A. niger* acid stable alpha-amylase, *A. niger* glucoamylase, *Rhizomucor miehei* lipase, *A. oryzae* alkaline protease or *A. oryzae* triose phosphate isomerase.

In particular when the host organism is *A. oryzae*, a preferred promoter for use in the process of the present invention is the *A. oryzae* TAKA amylase promoter as it exhibits a strong transcriptional activity in *A. oryzae*. The sequence of the TAKA amylase promoter appears from EP 238 023.

Termination and polyadenylation sequences may suitably be derived from the same sources as the promoter.

To ensure secretion of the inhibitor or variants hereof from the host cell, the DNA sequence encoding the inhibitor may be preceded by a signal sequence which may be a naturally occurring signal sequence or a functional part thereof or a synthetic sequence providing secretion of the protein from the cell. In particular, the signal sequence may be derived from a gene encoding an *Aspergillus sp.* amylase or glucoamylase, a gene encoding a *Rhizomucor miehei* lipase or proteinase, or a gene encoding a Humicola cellulase, xylanase or lipase.

Detergent

The detergent of the invention may be in any convenient form, e.g. powder, granules or liquid. A liquid detergent may be aqueous, typically containing 20–70% water and 0–20% organic solvent.

The detergent comprises surfactant which may be anionic, non-ionic, cationic, amphoteric or a mixture of these types. The detergent will usually contain 5–30% anionic surfactant such as linear alkyl benzene sulphonate (LAS), alpha-olefin sulphonate (AOS), alcohol ethoxy sulphate (AES) or soap. It may also contain 3–20% anionic surfactant such as nonyl phenol ethoxylate or alcohol ethoxylate.

The pH (measured in aqueous detergent solution) will usually be neutral or alkaline, e.g. 7–10. The detergent may contain 1–40% of a detergent builder such as zeolite, phosphate, phosphonate, citrate, NTA, EDTA or DTPA, or it may be unbuilt (i.e. essentially free of a detergent builder). It may also contain other conventional detergent ingredients, e.g. fabric conditioners, foam boosters, bactericides, optical brighteners and perfumes.

Specific examples of detergents according to the invention may be obtained from the compositions disclosed in WO 89/04361, DE 5111/89 or PCT/DK91/00243 by incorporating protease and inhibitor according to the invention. PCT/DK91/00243 is incorporated herein by reference.

The invention is particularly applicable to the formulation of liquid detergents with pronounced enzyme stability problems, e.g. those containing oxidizing agents. Such detergents typically contain 1–40%, especially 5–20% oxidizing agent. They may be granular detergents containing granules of a perborate or percarbonate and separate granules containing enzyme and inhibitor according to the invention, or they may be aqueous or non-aqueous liquid detergents containing hydrogen peroxide, a perborate or a percarbonate (see e.g. EP 378,261, EP 378,262, EP 294,904, EP 368,575).

Detergent Additive

The protease and inhibitor may be included in the detergent of the invention by separate addition or by adding the combined additive provided by the invention. The additive will usually contain 0.2–8 mM protease (0.5–20%) and have an inhibitor/protease ratio as described above.

The detergent additive may be in liquid form for incorporation in a liquid detergent. A liquid additive may contain 20–90% propylene glycol; 0.5–3% (as Ca) of a soluble calcium salt; 0–10% glycerol; minor amounts of short-chain fatty acids and carbohydrate; and water up to 100%.

EXAMPLE 1

Expression of Barley Subtilisin Inhibitor CI-2 in *Saccharomyces cerevisiae*

The barley subtilisin inhibitor and variants thereof according to the invention can be produced biosynthetically in a yeast host expressing a DNA sequence encoding the inhibitor.

To achieve secretion to the growth medium, the DNA sequence encoding the inhibitor can be fused to another DNA-sequence encoding a signal peptide functional in yeast. An example thereof is the *Saccharomyces cerevisiae* MF-alpha-1 leader sequence (Kurjan & Herskowitz, Cell 30, 933–943 (1982). A preferred construction uses the DNA generated, which contained the desired mutations. The ends were trimmed with the restriction enzymes KpnI and XbaI, purified on agarose gels, and cloned into pYACI2 previously digested with the same restriction enzymes. The presence of the mutation was verified by DNA sequencing. The primers used are listed below.

| Mutation | Primer sequence | |
|---|---|---|
| P4 Ile —> Pro | 5'-CCGGTGGGTACCCCAGTGACCATGGAA-3' | (SEQ ID NO: 12) |
| P4 Ile —> Trp | 5'-CCGGTGGGTACCTGGGTGACCATGGAA-3' | (SEQ ID NO: 18) |
| P3 Val —> Glu | 5'-GTGGGTACCATTGAAACCATGGAATAT-3' | (SEQ ID NO: 13) |
| P3 Val —> Ala | 5'-GTGGGTACCATTGCTACCATGGAATAT-3' | (SEQ ID NO: 19) |
| P3 Val —> Arg | 5'-GTGGGTACCATTAGAACCATGGAATAT-3' | (SEQ ID NO: 20) |
| P3 Val —> Tyr | 5'-GTGGGTACCATTTACACCATGGAATAT-3' | (SEQ ID NO: 21) |
| P3 Val —> Pro | 5'-GTGGGTACCATTCCAACCATGAAGTAT-3' | (SEQ ID NO: 22) |
| P2 Thr —> Glu | 5'-GTGGGTACCATTGTGGAAATGGAATATCGG-3' | (SEQ ID NO: 14) |
| P2 Thr —> Val | 5'-GTGGGTACCATTGTGGTTATGGAATATCGG-3' | (SEQ ID NO: 23) |
| P2 Thr —> Arg | 5'-GTGGGTACCATTGTGAGAATGGAATATCGG-3' | (SEQ ID NO: 24) |
| P2 Thr —> Tyr | 5'-GTGGGTACCATTGTGTACATGGAATATCGG-3' | (SEQ ID NO: 25) |
| P2 Thr —> Pro | 5'-GTGGGTACCATTGTGCCAATGGAATATCGG-3' | (SEQ ID NO: 26) |
| P1 Met —> Glu | 5'-GTGGGTACCATTGTGACCGAAGAATATCGGATC-3' | (SEQ ID NO: 15) |
| P1 Met —> Val | 5'-GTGGGTACCATTGTGACCGTTGAATATCGGATC-3' | (SEQ ID NO: 27) |
| P1 Met —> Arg | 5'-GTGGGTACCATTGTGACCAGAGAATATCGGATC-3' | (SEQ ID NO: 28) |
| P1 Met —> Tyr | 5'-GTGGGTACCATTGTGACCTACGAATATCGGATC-3' | (SEQ ID NO: 29) |
| P1 Met —> Pro | 5'-GTGGGTACCATTGTGACCCCAGAATATCGGATC-3' | (SEQ ID NO: 30) | sequence encoding the entire 85 amino acid MF-alpha-1 leader sequence including the dibasic site LysArg. In that way, an efficient secretion of CI-2 inhibitor with the correct N-terminal is achieved.

Plasmid construction

All expression plasmids are of the C-POT type. Such plasmids are described in EP patent application No. 85303702.6 and are characterized in containing the *S. pombe* triose phosphate isomerase gene (POT) for the purpose of plasmid stabilization. A plasmid containing the POT-gene is available from a deposited *E.coli* strain (ATCC 39685). The plasmids furthermore contain the *S. cerevisiae* triose phosphate isomerase promoter and terminater ($P_{TPI}$ and $T_{TPI}$). They are identical to pLaC200 described in the patent application WO 89/02463, except for the region defined by the EcoRI/XbaI restriction fragment encoding a signal/leader/insulin precursor sequence. In this application, the region is replaced by a fragment encoding MF-alpha-1 leader fused to the inhibitor sequence. The sequence of the fragment is SEQ ID No. 1 (P1 is located at Met 59). The isolation of the barley CI-2 subtilisin inhibitor cDNA is described by Williamson et al. Eur. J. Biochem. 165, 99–106 (1987). Cloning of the MF-alpha-1 leader is described by Kurjan & Herskowitz (reference given above). Modifications and assembly of the two sequences were carried out using entirely standard techniques. In particular, the KpnI and ClaI restriction sites at positions 495 and 519, respectively, were generated by introducing silent mutations into the inhibitor gene. This was done carrying out in vitro mutagenesis on the inhibitor gene. A map of the expression plasmid pYACI2 is shown in FIG. 1.

Introduction of Mutations into the Inhibitor Gene

Mutant CI-2 genes were generated using PCR mutagenesis, which was carried out as follows: A primer carrying the mutation flanked by homologous sequences and carrying the introduced KpnI-site was used together with another primer homologous to sequences in the $T_{TPI}$ region in a PCR amplification reaction. In that way, fragments were The primer sequence used for the generation of the P4 mutation (Ile→Pro and Ile→Trp) is listed in the Sequence Listing as SEQ ID NO: 12; the primer sequence used for the generation of the P3 mutation (Val→Glu, Val→Ala, Val→Arg, Val→Tyr, and Val→Pro) is listed in the Sequence Listing as SEQ ID NO: 13; the primer sequence used for the generation of the P2 mutation (Thr→Glu, Thr→Val, Thr→Arg, Thr→Tyr, and Thr→Pro) is listed in the Sequence Listing as SEQ ID NO: 14; and the primer sequence used for the generation of the P1 mutation (Met→Glu, Met→Val, Met→Arg, and Met→Tyr) is listed in the Sequence Listing as SEQ ID NO: 15.

The sequence of the other primer used for generation of PCR products, and which has homology to the $T_{TPI}$ terminater region is: 5'-TTAAGTGGCTCAGAATG-3' (SEQ ID NO: 31)

Expression of Mutant CI-2 Inhibitors in Yeast

Plasmids prepared as described above were transformed into a *S. cerevisiae* strain carrying deletions in the TPI gene by selecting for growth on glucose.

The transformed yeast strains were grown on YPD medium (Sherman, F. et al., Methods in Yeast Genetics, Cold Spring Harbor Laboratory 1981). 100 ml medium in shake-flasks was inoculated with individual transformants and shaken at 30° C. for approx. 48 hours after which the inhibitor could be purified from the medium.

EXAMPLE 2

Expression of Barley Subtilisin Inhibitor CI-2 CI-2A in *Aspergillus oryzae*

Plasmid constructions

Cloning and expression of *Humicola lanuginosa* lipase in *Aspergillus oryzae* is described in EP 305,216. The same host/vector system can be used for expression and secretion of barley subtilisin inhibitor CI-2 CI-2A. The lipase expression plasmid is termed p960 and makes use of the *A. oryzae* TAKA amylase promoter for driving the transcription and the *Aspergillus niger* glucoamylase transcription terminater.

Figure 2:
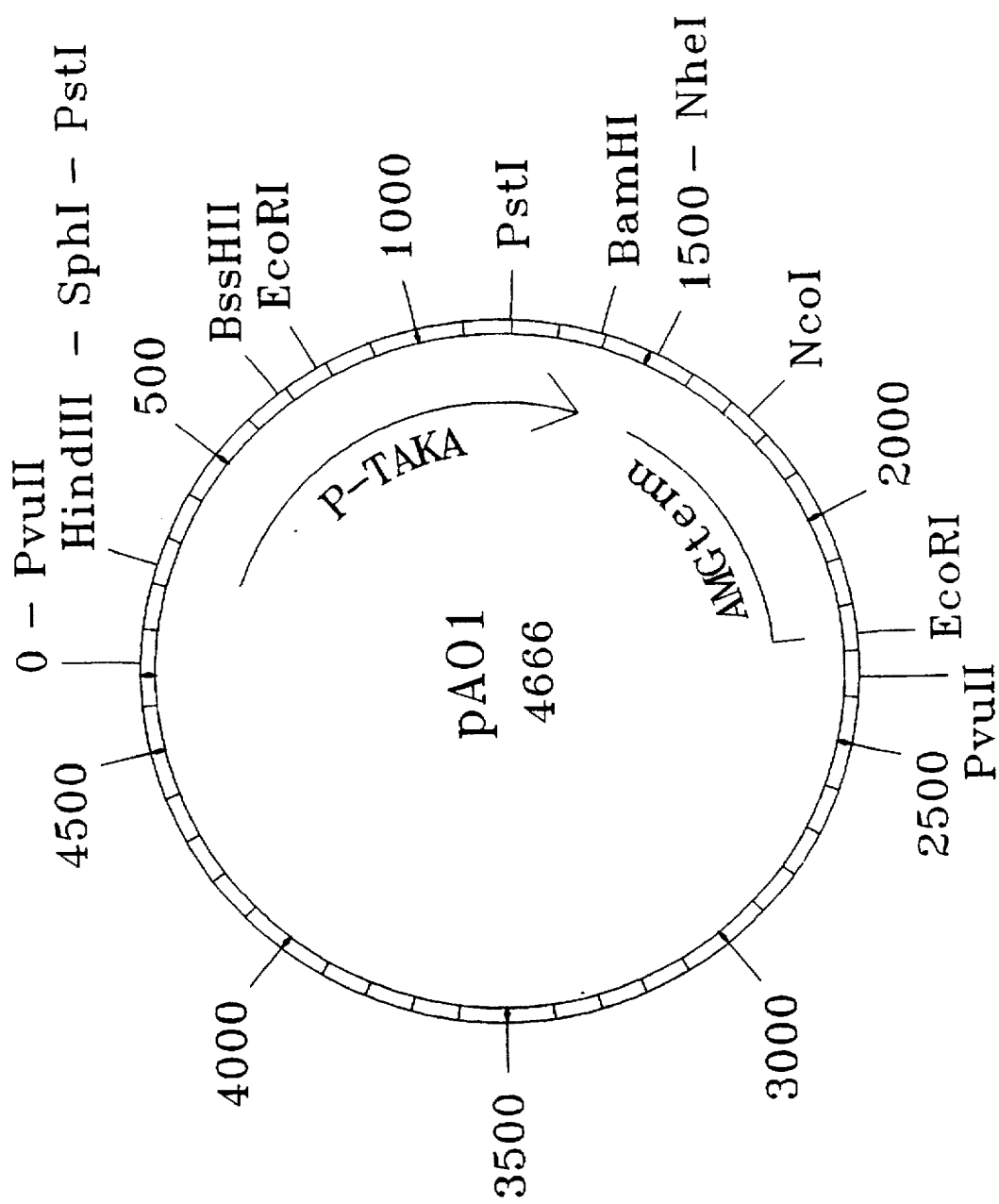
FIG. 2 shows a map of the expression plasmid pAO1.

The plasmid p960 was slightly modified in order to obtain a vector for cloning the inhibitor gene. p960 was digested with NruI and BamHI restriction enzymes. Between these two sites the BamHI/NheI fragment from pBR322, in which the NheI-site was filled in with Klenow polymerase and dNTP's, was cloned, thereby creating plasmid pAO1 (FIG. 2) which contains unique BamHI and NheI sites facilitating cloning of BamHI/XbaI fragments.

A BamHI/AvaI linker with the sequence

GATCC ACC ATG AGG AGC TCC CTT GTG CTG TTC TTT GTC TCT GCG TGG ACG GCC TTG GCC AGT C

GTGG TAC TCC TCG AGG GAA CAG GAC AAG AAA CAG AGA CGC ACC TGC CGG AAC CGG TCA G

Met Arg Ser Ser Leu Val Leu Phe Phe Val Ser Ala Trp Thr Ala Leu Ala Ser P

CT ATT CGT CGA AGC TCA GTG GAG AAG AAGC    AvaI

GATAA GCA GCT TCG AGT CAC CTC TTC TTC GGGCT ro Ile Arg Arg Ser Ser Val Glu Lys Lys Pro

Figure 3:
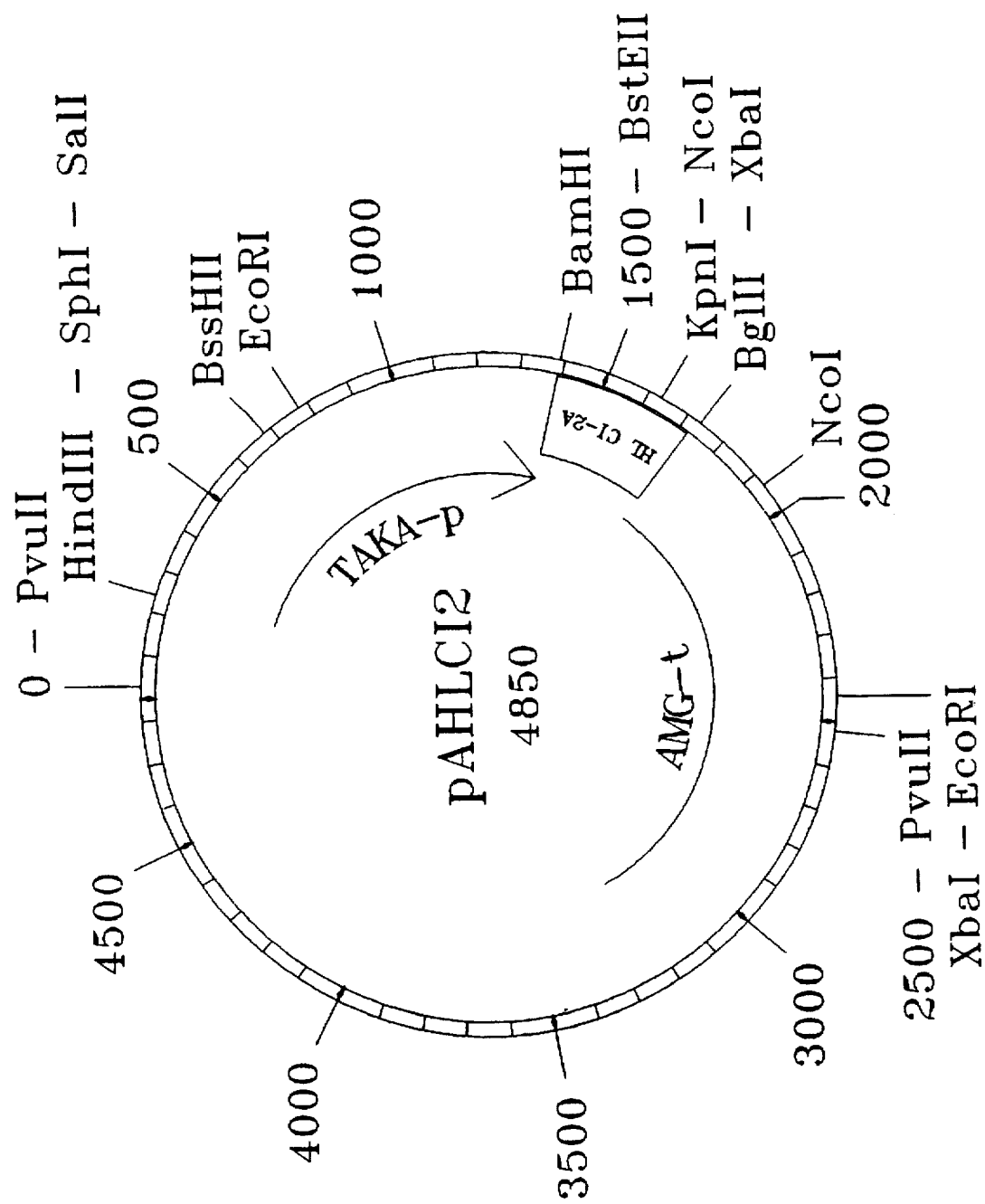
FIG. 3 shows a map of the expression plasmid pAHLCI2.

The BamHI/AvaI linker sequence is listed in the Sequence Listing as SEQ ID NO: 16 (5'–3' strand and amino acid sequence) and SEQ ID NO: 17 (3'–5' strand). Encoding the *Humicola lanuginosa* lipase pre-pro sequence and part of the CI-2 inhibitor was combined with the AvaI/XbaI fragment from pYACI2 and cloned into pAO1 digested with BamHI and NheI, thereby creating the expression plasmid pAHLCI2 (FIG. 3). The sequence of the BamHI/XbaI insert is SEQ ID No. 3 (P1 at Met 59).

Transformation of *Aspergillus oryzae* (general procedure)

100 ml of YPD (Sherman et al., Methods in Yeast Genetics, Cold Spring Harbor Laboratory, 1981) was inoculated with spores of *A. oryzae* and incubated with shaking for about 24 hours. The mycelium was harvested by filtration through miracloth and washed with 200 ml of 0.6M MgSO$_4$. The mycelium was suspended in 15 ml of 1.2M MgSO$_4$, 10 mMNaH$_2$PO$_4$, pH=5.8. The suspension was cooled on ice and 1 ml of buffer containing 120 mg of Novozym® 234, batch 1687 was added. After 5 min., 1 ml of 12 mg/ml BSA (Sigma type H25) was added and incubation with gentle agitation continued for 1.5–2.5 hours at 37° C. until a large number of protoplasts was visible in a sample inspected under the microscope.

The suspension was filtered through miracloth, the filtrate transferred to a sterile tube and overlayed with 5 ml of 0.6M sorbitol, 100 mM Tris-HCl, pH=7.0. Centrifugation was performed for 15 min. at 1000 g and the protoplasts were collected from the top of the MgSO$_4$ cushion. 2 volumes of STC (1.2M sorbitol, 10 mM Tris-HCl, pH=7.5, 10 mM CaCl$_2$) were added to the protoplast suspension and the mixture was centrifugated for 5 min. at 1000 g. The protoplast pellet was resuspended in 3 ml of STC and repelleted. This was repeated. Finally, the protoplasts were resuspended in 0.2–1 ml of STC.

100 µl of protoplast suspension was mixed with 5–25 µg of p3SR2 (an *A. nidulans* amdS gene carrying plasmid described in Hynes et al., Mol. and Cel. Biol., Vol. 3, No. 8, 1430–1439, Aug. 1983) in 10 µl of STC. The mixture was left at room temperature for 25 min. 0.2 ml of 60% PEG 4000 (BDH 29576), 10 mM CaCl$_2$ and 10 mM Tris-HCl, pH=7.5 was added and carefully mixed (twice) and finally 0.85 ml of the same solution was added and carefully mixed. The mixture was left at room temperature for 25 min., spun at 2.500 g for 15 min. and the pellet was resuspended in 2 ml of 1.2M sorbitol. After one more sedimentation the protoplasts were spread on minimal plates (Cove, Biochem. Biophys. Acta 113 (1966) 51–56) containing 1.0M sucrose, pH=7.0, 10 mM acetamide as nitrogen source and 20 mM CsCl to inhibit background growth. After incubation for 4–7 days at 37° C. spores were picked, suspended in sterile water and spread for single colonies. This procedure was repeated and spores of a single colony after the second reisolation were stored as a defined transformant.

Expression of the Barley Inhibitor CI-2 in *A. oryzae* pAHLCI2 was transformed into *A. oryzae* IFO 4177 by cotransformation with p3SR2 containing the amdS gene from *A. nidulans* as described above. Protoplasts prepared as described were incubated with a mixture of equal amounts of pAHLCI2 and p3SR2, approximately 5 µg of each were used. 9 transformants which could use acetamide as sole nitrogen source were reisolated twice. After growth on YPD for three days, culture supernatants were analyzed for inhibitor activity.

EXAMPLE 3

Purification of the Wild-Type CI-2 Inhibitor and Mutants Thereof

Fermentation broths containing either the wild-type CI-2 inhibitor or one of the following CI-2 inhibitor mutants: CI-2 (M59P), CI-2 (V57E), CI-2 (M59E), CI-2 (M59R), CI-2 (V57R) and CI-2(V57P+E60K), produced as described in example 1, were filtered on a pressure filter (Zeitz K 250-Neu) provided with 0.5% filter aid, and subsequently on a Zeitz EK-1 filter provided with 0.5% filter aid. The filtrate was diluted to a conductivity of <4 mS with 50 mM sodium acetate, pH 4.4, and water, and the pH was adjusted to 4.4. The filtrate was then subjected to chromatography on a S-Sepharose FPLC column using a 50 mM sodium acetate buffer, pH 4.4, and a 50 mM sodium acetate buffer supplemented with 1M NaCl. Elution of the column was performed with a 0–100% gradient of 50 mM sodium acetate buffer supplemented with 1M NaCl.

To effect a change of buffer, the eluate was run through a Sephadex G-25 column into two different buffers: (a) 50 mM glycine-NaOH buffer, pH 9.6, and (b) 50 mM H$_3$BO$_3$—NaOH buffer, pH 10.2 (buffer (b) being used for basic mutants (CI-2(M59R), CI-2(V57R) and CI-2(V57P+E60K) ). The eluate was then subjected to chromatography on a Q-Sepharose column using either buffer (a) or buffer (b), as appropriate. The column was eluted with a gradient of 0–1M NaCl. Inhibitor-containing fractions were collected and used in the subsequent experiments.

EXAMPLE 4

Interaction of Protease with Inhibitor

The interaction of Alcalase® with wild-type CI-2, CI-2 (M59P) and CI-2(V57E), respectively, was studied in a 0.1M Tris—HCl buffer, pH 8.6, at 25° C., using the synthetic peptide substrates Suc—Ala—Ala—Pro—Phe—pNA and Suc—Ala—Ala—Ala—pNA (both available from Sigma) to determine residual activity after reacting the protease with the inhibitor in amounts from 0 to 1.5 times the protease concentration.

The following dissociation constants were determined using non-linear regression essentially as described in M. Tashiro et al., *Agric. Biol. Chem.* 55(1), 1991, pp. 265–267.

| Inhibitor | Dissociation constant ($K_d$) |
| --- | --- |
| Wild-type CI-2 | $4 \times 10^{-12}$M |
| CI-2(M59P) (mutated in P1) | $5 \times 10^{-9}$M |
| CI-2(V57E) (mutated in P3) | $1 \times 10^{-10}$M |

The results show that it is possible to change the dissociation constant by several orders of magnitude by single amino acid substitutions in the binding region of the inhibitor.

We claim:

1. A modified protease inhibitor, comprising an amino acid sequence of a protease inhibitor selected from the group consisting of Eglin B, Eglin C, barley subtilisin inhibitor CI-2, barley subtilisin inhibitor CI-1, potato subtilisin inhibitor, tomato subtilisin inhibitor, and Vicia subtilisin inhibitor, wherein the amino acid sequence is substituted at one or more of the following positions of the binding domain with:

P4: an amino acid selected from the group consisting or Val, Pro, Trp, Ser, Glu and Arg;

P3: an amino acid selected from the group consisting of Tyr, Glu, Ala, Arg, Pro, Ser, Lys and Trp;

P2: an amino acid selected from the group consisting of Lys, Arg, Glu, Val, Tyr, Trp and Ala; and P1: an amino acid selected from the group consisting of Pro, Trp, Glu, Val and Ser.

2. A modified protease inhibitor according to claim 1, wherein the amino acid sequence is substituted at position P4.

3. A modified protease inhibitor according to claim 1, wherein the amino acid sequence is substituted at position P3.

4. A modified protease inhibitor according to claim 1, wherein the amino acid sequence is substituted at position P2.

5. A modified protease inhibitor according to claim 1, wherein the amino acid sequence is substituted at position P1.

6. The modified protease inhibitor according to claim 1, wherein the protease inhibitor is Eglin B.

7. The modified protease inhibitor according to claim 1, wherein the protease inhibitor is Eglin C.

8. The modified protease inhibitor according to claim 1, wherein the protease inhibitor is barley subtilisin inhibitor CI-2.

9. The modified protease inhibitor according to claim 8, wherein the amino acid sequence is substituted at position P1 of the binding domain with Pro.

10. The modified protease inhibitor according to claim 8, wherein the amino acid sequence is substituted at position P3 of the binding domain with Glu.

11. The modified protease inhibitor according to claim 8, wherein the amino acid sequence is substituted at position P1 of the binding domain with Glu.

12. The modified protease inhibitor according to claim 8, wherein the amino acid sequence is substituted at position P1 of the binding domain with Arg.

13. The modified protease inhibitor according to claim 8, wherein the amino acid sequence is substituted at position P3 of the binding domain with Arg.

14. The modified protease inhibitor according to claim 8, wherein the amino acid sequence is substituted at position P3 of the binding domain with Pro and at position P'1 of the binding domain with Lys.

15. The modified protease inhibitor according to claim 1, wherein the protease inhibitor is barley subtilisin inhibitor CI-1.

16. The modified protease inhibitor according to claim 1, wherein the protease inhibitor is potato subtilisin inhibitor.

17. The modified protease inhibitor according to claim 1, wherein the protease inhibitor is tomato subtilisin inhibitor.

18. The modified protease inhibitor according to claim 1, wherein the protease inhibitor is Vicia subtilisin inhibitor.

19. A detergent composition comprising a protease, a modified protease inhibitor according to claim 1 and a surfactant.

20. The detergent composition according to claim 19 which is in liquid form.

21. The detergent composition according to claim 19, wherein the protease is a serine protease.

22. The detergent composition according to claim 21, wherein the protease is an alkaline microbial protease or a trypsin protease.

23. The detergent composition according to claim 22, wherein the protease is trypsin or is derived from a protease producing strain of Fusarium.

24. The detergent composition according to claim 22, wherein the protease is a subtilisin.

25. The detergent composition according to claim 24, wherein the subtilisin is derived from a protease producing strain of Bacillus.

26. The detergent composition according to claim 25, wherein the subtilisin is selected from the group consisting of Subtilisin Novo, Subtilisin Carlsberg, Subtilisin BPN', Subtilisin 309, Subtilisin 147 and Subtilisin 168.

27. A detergent additive comprising a protease and a reversible protease inhibitor according to claim 21, wherein the detergent additive is in the form selected from the group consisting of a non-dusting granulate, a liquid, a slurry and a protected enzyme.

* * * * *

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 592 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: barley ( i x ) FEATURE:
        ( A ) NAME/KEY: CDS
        ( B ) LOCATION: 77..580

( i x ) FEATURE:
        ( A ) NAME/KEY: sig_peptide
        ( B ) LOCATION: 77..331

( i x ) FEATURE:
        ( A ) NAME/KEY: mat_peptide
        ( B ) LOCATION: 33(2)..580

( x i ) SEQUENCE DESCRIPTION: SEQ ID NO:1:

```
GAATTCCATT CAAGAATAGT TCAAACAAGA AGATTACAAA CTATCAATTT CATACACAAT          60

ATAAACGATT AAAAGA ATG AGA TTT CCT TCA ATT TTT ACT GCA GTT TTA            109
               Met Arg Phe Pro Ser Ile Phe Thr Ala Val Leu
               -85             -80                 -75

TTC GCA GCA TCC TCC GCA TTA GCT GCT CCA GTC AAC ACT ACA ACA GAA          157
Phe Ala Ala Ser Ser Ala Leu Ala Ala Pro Val Asn Thr Thr Thr Glu
            -70             -65                 -60

GAT GAA ACG GCA CAA ATT CCG GCT GAA GCT GTC ATC GGT TAC TCA GAT          205
Asp Glu Thr Ala Gln Ile Pro Ala Glu Ala Val Ile Gly Tyr Ser Asp
        -55             -50                 -45

TTA GAA GGG GAT TTC GAT GTT GCT GTT TTG CCA TTT TCC AAC AGC ACA          253
Leu Glu Gly Asp Phe Asp Val Ala Val Leu Pro Phe Ser Asn Ser Thr
    -40             -35                 -30

AAT AAC GGG TTA TTG TTT ATA AAT ACT ACT ATT GCC AGC ATT GCT GCT          301
Asn Asn Gly Leu Leu Phe Ile Asn Thr Thr Ile Ala Ser Ile Ala Ala
-25             -20                 -15

AAA GAA GAA GGG GTA TCT TTG GAT AAA AGA AGT TCA GTG GAG AAG AAG          349
Lys Glu Glu Gly Val Ser Leu Asp Lys Arg Ser Ser Val Glu Lys Lys
```

-continued

```
       -10                           -5                            1                            5
CCC   GAG   GGA   GTG   AAC   ACC   GGT   GCT   GGT   GAC   CGT   CAC   AAC   CTG   AAG   ACA           397
Pro   Glu   Gly   Val   Asn   Thr   Gly   Ala   Gly   Asp   Arg   His   Asn   Leu   Lys   Thr
                   10                      15                      20

GAG   TGG   CCA   GAG   TTG   GTG   GGG   AAA   TCG   GTG   GAG   GAG   GCC   AAG   AAG   GTG           445
Glu   Trp   Pro   Glu   Leu   Val   Gly   Lys   Ser   Val   Glu   Glu   Ala   Lys   Lys   Val
             25                            30                            35

ATT   CTG   CAG   GAC   AAG   CCA   GAG   GCG   CAA   ATC   ATA   GTT   CTG   CCG   GTG   GGT           493
Ile   Leu   Gln   Asp   Lys   Pro   Glu   Ala   Gln   Ile   Ile   Val   Leu   Pro   Val   Gly
       40                            45                            50

ACC   ATT   GTG   ACC   ATG   GAA   TAT   CGG   ATC   GAT   CGC   GTC   CGC   CTC   TTT   GTC           541
Thr   Ile   Val   Thr   Met   Glu   Tyr   Arg   Ile   Asp   Arg   Val   Arg   Leu   Phe   Val
 55                             60                            65                            70

GAT   AAA   CTC   GAC   AAC   ATT   GCC   CAG   GTC   CCT   AGG   GTC   GGC   TAGTGATCTA                  590
Asp   Lys   Leu   Asp   Asn   Ile   Ala   Gln   Val   Pro   Arg   Val   Gly
                   75                            80

GA                                                                                                        592
```

( 2 ) INFORMATION FOR SEQ ID NO:2:

( i ) SEQUENCE CHARACTERISTICS:
      ( A ) LENGTH: 168 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

```
Met   Arg   Phe   Pro   Ser   Ile   Phe   Thr   Ala   Val   Leu   Phe   Ala   Ala   Ser   Ser
-85                            -80                           -75                           -70

Ala   Leu   Ala   Ala   Pro   Val   Asn   Thr   Thr   Thr   Glu   Asp   Glu   Thr   Ala   Gln
                         -65                           -60                           -55

Ile   Pro   Ala   Glu   Ala   Val   Ile   Gly   Tyr   Ser   Asp   Leu   Glu   Gly   Asp   Phe
                  -50                           -45                           -40

Asp   Val   Ala   Val   Leu   Pro   Phe   Ser   Asn   Ser   Thr   Asn   Asn   Gly   Leu   Leu
             -35                           -30                           -25

Phe   Ile   Asn   Thr   Thr   Ile   Ala   Ser   Ile   Ala   Ala   Lys   Glu   Glu   Gly   Val
-20                                  -15                           -10

Ser   Leu   Asp   Lys   Arg   Ser   Ser   Val   Glu   Lys   Lys   Pro   Glu   Gly   Val   Asn
 -5                      1                       5                                     10

Thr   Gly   Ala   Gly   Asp   Arg   His   Asn   Leu   Lys   Thr   Glu   Trp   Pro   Glu   Leu
                   15                            20                            25

Val   Gly   Lys   Ser   Val   Glu   Glu   Ala   Lys   Lys   Val   Ile   Leu   Gln   Asp   Lys
             30                            35                            40

Pro   Glu   Ala   Gln   Ile   Ile   Val   Leu   Pro   Val   Gly   Thr   Ile   Val   Thr   Met
 45                            50                            55

Glu   Tyr   Arg   Ile   Asp   Arg   Val   Arg   Leu   Phe   Val   Asp   Lys   Leu   Asp   Asn
 60                      65                            70                            75

Ile   Ala   Gln   Val   Pro   Arg   Val   Gly
                         80
```

( 2 ) INFORMATION FOR SEQ ID NO:3:

( i ) SEQUENCE CHARACTERISTICS:
      ( A ) LENGTH: 336 base pairs
      ( B ) TYPE: nucleic acid
      ( C ) STRANDEDNESS: single
      ( D ) TOPOLOGY: linear ( i i ) MOLECULE TYPE: cDNA ( v i ) ORIGINAL SOURCE:
  ( A ) ORGANISM: barley ( i x ) FEATURE:
  ( A ) NAME/KEY: CDS
  ( B ) LOCATION: 10..324

( i x ) FEATURE:
  ( A ) NAME/KEY: sig_peptide
  ( B ) LOCATION: 10..75

( i x ) FEATURE:
  ( A ) NAME/KEY: mat_peptide
  ( B ) LOCATION: 76..324

( x i ) SEQUENCE DESCRIPTION: SEQ ID NO:3:

```
GGATCCACC ATG AGG AGC TCC CTT GTG CTG TTC TTT GTC TCT GCG TGG              48
          Met Arg Ser Ser Leu Val Leu Phe Phe Val Ser Ala Trp
          -22     -20             -15                     -10

ACG GCC TTG GCC AGT CCT ATT CGT CGA AGC TCA GTG GAG AAG AAG CCC            96
Thr Ala Leu Ala Ser Pro Ile Arg Arg Ser Ser Val Glu Lys Lys Pro
             -5              1               5

GAG GGA GTG AAC ACC GGT GCT GGT GAC CGT CAC AAC CTG AAG ACA GAG           144
Glu Gly Val Asn Thr Gly Ala Gly Asp Arg His Asn Leu Lys Thr Glu
         10              15                      20

TGG CCA GAG TTG GTG GGG AAA TCG GTG GAG GAG GCC AAG AAG GTG ATT           192
Trp Pro Glu Leu Val Gly Lys Ser Val Glu Glu Ala Lys Lys Val Ile
     25              30              35

CTG CAG GAC AAG CCA GAG GCG CAA ATC ATA GTT CTG CCG GTG GGT ACC           240
Leu Gln Asp Lys Pro Glu Ala Gln Ile Ile Val Leu Pro Val Gly Thr
 40              45                      50                  55

ATT GTG ACC ATG GAA TAT CGG ATC GAT CGC GTC CGC CTC TTT GTC GAT           288
Ile Val Thr Met Glu Tyr Arg Ile Asp Arg Val Arg Leu Phe Val Asp
                 60              65                      70

AAA CTC GAC AAC ATT GCC CAG GTC CCT AGG GTC GGC TAGTGATCTA                334
Lys Leu Asp Asn Ile Ala Gln Val Pro Arg Val Gly
             75              80

GA                                                                        336
```

( 2 ) INFORMATION FOR SEQ ID NO:4:

( i ) SEQUENCE CHARACTERISTICS:
    ( A ) LENGTH: 105 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

```
Met Arg Ser Ser Leu Val Leu Phe Phe Val Ser Ala Trp Thr Ala Leu
-22     -20             -15                     -10

Ala Ser Pro Ile Arg Arg Ser Ser Val Glu Lys Lys Pro Glu Gly Val
     -5              1               5                      10

Asn Thr Gly Ala Gly Asp Arg His Asn Leu Lys Thr Glu Trp Pro Glu
             15                      20                  25

Leu Val Gly Lys Ser Val Glu Glu Ala Lys Lys Val Ile Leu Gln Asp
             30              35                      40

Lys Pro Glu Ala Gln Ile Ile Val Leu Pro Val Gly Thr Ile Val Thr
         45              50                  55

Met Glu Tyr Arg Ile Asp Arg Val Arg Leu Phe Val Asp Lys Leu Asp
     60              65                      70

Asn Ile Ala Gln Val Pro Arg Val Gly
 75              80
```

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Asp Ala Met Val His Leu Asn Phe Asp
1               5

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

Gly Thr Ile Val Thr Met Glu Tyr Arg
1               5

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

Gly Ser Pro Val Thr Met Asp Phe Arg
1               5

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

Gly Ser Pro Val Thr Leu Asp Leu Arg
1               5

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Gly Ser Pro Val Thr Leu Asp Leu Arg
1               5

( 2 ) INFORMATION FOR SEQ ID NO:10:

( i ) SEQUENCE CHARACTERISTICS:
        ( A ) LENGTH: 9 amino acids (B) TYPE: amino acid
(D) TOPOLOGY: linear (ii) MOLECULE TYPE: peptide (xi) SEQUENCE DESCRIPTION: SEQ ID NO:10:

Gly Ser Pro Ile Thr Leu Asp Tyr Leu
1               5

(2) INFORMATION FOR SEQ ID NO:11:

(i) SEQUENCE CHARACTERISTICS:
    (A) LENGTH: 9 amino acids
    (B) TYPE: amino acid
    (D) TOPOLOGY: linear (ii) MOLECULE TYPE: peptide (xi) SEQUENCE DESCRIPTION: SEQ ID NO:11:

Gly Ser Phe Val Thr Ala Asp Tyr Lys
1               5

(2) INFORMATION FOR SEQ ID NO:12:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:12:

CCGGTGGGTA CCCCAGTGAC CATGGAA                                    27

(2) INFORMATION FOR SEQ ID NO:13:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:13:

GTGGGTACCA TTGAAACCAT GGAATAT                                    27

(2) INFORMATION FOR SEQ ID NO:14:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:14:

GTGGGTACCA TTGTGGAAAT GGAATATCGG                                 30

(2) INFORMATION FOR SEQ ID NO:15:

(i) SEQUENCE CHARACTERISTICS:
    (A) LENGTH: 33 base pairs
    (B) TYPE: nucleic acid
    (C) STRANDEDNESS: single
    (D) TOPOLOGY: linear (ii) MOLECULE TYPE: cDNA ( x i ) SEQUENCE DESCRIPTION: SEQ ID NO:15:

GTGGGTACCA TTGTGACCGA AGAATATCGG ATC                                      33

( 2 ) INFORMATION FOR SEQ ID NO:16:

( i ) SEQUENCE CHARACTERISTICS:
        ( A ) LENGTH: 93 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

```
GATCCACC ATG AGG AGC TCC CTT GTG CTG TTC TTT GTC TCT GCG TGG ACG          50
         Met Arg Ser Ser Leu Val Leu Phe Phe Val Ser Ala Trp Thr
         1            5                        10

GCC TTG GCC AGT CCT ATT CGT CGA AGC TCA GTG GAG AAG AAG C                 93
Ala Leu Ala Ser Pro Ile Arg Arg Ser Ser Val Glu Lys Lys Pro
15                  20                  25                  30
```

( 2 ) INFORMATION FOR SEQ ID NO:17:

( i ) SEQUENCE CHARACTERISTICS:
        ( A ) LENGTH: 93 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

GTGGTACTCC TCGAGGGAAC ACGACAAGAA ACAGAGACGC ACCTGCCGGA ACCGGTCAGG          60

ATAAGCAGCT TCGAGTCACC TCTTCTTCGG GCT                                      93

( 2 ) INFORMATION FOR SEQ ID NO:18:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

CCGGTGGGTA CCTGGGTGAC CATGGAA                                             27

( 2 ) INFORMATION FOR SEQ ID NO:19:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

GTGGGTACCA TTGCTACCAT GGAATAT                                             27

( 2 ) INFORMATION FOR SEQ ID NO:20:

( i ) SEQUENCE CHARACTERISTICS:
        ( A ) LENGTH: 27 base pairs
        ( B ) TYPE: nucleic acid
        ( C ) STRANDEDNESS: single (D) TOPOLOGY: linear (i i) MOLECULE TYPE: cDNA (x i) SEQUENCE DESCRIPTION: SEQ ID NO:20:

GTGGGTACCA TTAGAACCAT GGAATAT    27

(2) INFORMATION FOR SEQ ID NO:21:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (i i) MOLECULE TYPE: cDNA (x i) SEQUENCE DESCRIPTION: SEQ ID NO:21:

GTGGGTACCA TTTACACCAT GGAATAT    27

(2) INFORMATION FOR SEQ ID NO:22:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (i i) MOLECULE TYPE: cDNA (x i) SEQUENCE DESCRIPTION: SEQ ID NO:22:

GTGGGTACCA TTCCAACCAT GAAGTAT    27

(2) INFORMATION FOR SEQ ID NO:23:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (i i) MOLECULE TYPE: cDNA (x i) SEQUENCE DESCRIPTION: SEQ ID NO:23:

GTGGGTACCA TTGTGGTTAT GGAATATCGG    30

(2) INFORMATION FOR SEQ ID NO:24:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (i i) MOLECULE TYPE: cDNA (x i) SEQUENCE DESCRIPTION: SEQ ID NO:24:

GTGGGTACCA TTGTGAGAAT GGAATATCGG    30

(2) INFORMATION FOR SEQ ID NO:25:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (i i) MOLECULE TYPE: cDNA (x i) SEQUENCE DESCRIPTION: SEQ ID NO:25:

GTGGGTACCA TTGTGTACAT GGAATATCGG                                    30

(2) INFORMATION FOR SEQ ID NO:26:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

GTGGGTACCA TTGTGCCAAT GGAATATCGG                                    30

(2) INFORMATION FOR SEQ ID NO:27:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

GTGGGTACCA TTGTGACCGT TGAATATCGG ATC                                33

(2) INFORMATION FOR SEQ ID NO:28:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

GTGGGTACCA TTGTGACCAG AGAATATCGG ATC                                33

(2) INFORMATION FOR SEQ ID NO:29:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

GTGGGTACCA TTGTGACCTA CGAATATCGG ATC                                33

(2) INFORMATION FOR SEQ ID NO:30:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

GTGGGTACCA TTGTGACCCC AGAATATCGG ATC                                33

(2) INFORMATION FOR SEQ ID NO:31:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:31:

TTAAGTGGCT CAGAATG    17